United States Patent [19]

Goldstein et al.

[11] Patent Number: 5,665,536
[45] Date of Patent: Sep. 9, 1997

[54] DIAGNOSTIC METHOD AND TEST KIT FOR THE SEROLOGICAL DETECTION OF THE AIDS VIRUS

[75] Inventors: Allan L. Goldstein, Washington, D.C.; Su-Sun Wang, Belmont, Calif.

[73] Assignee: Viral Technologies, Inc., Alexandria, Va.

[21] Appl. No.: 476,647

[22] Filed: Jun. 7, 1995

Related U.S. Application Data

[62] Division of Ser. No. 884,153, May 18, 1992, which is a continuation of Ser. No. 577,672, Sep. 5, 1990, abandoned, which is a division of Ser. No. 300,176, Jan. 23, 1989, Pat. No. 4,983,387, which is a continuation of Ser. No. 864,599, May 19, 1986, abandoned.

[51] Int. Cl.$^6$ .................................. C12Q 1/70
[52] U.S. Cl. .................. 435/5; 435/7.1; 435/7.92; 435/7.93; 435/7.94; 435/7.95; 435/974; 435/975; 436/516; 530/324; 530/826
[58] Field of Search ............ 435/5, 7.1, 7.92–7.95, 435/240.27, 974, 975; 436/516; 530/324, 826

[56] References Cited

U.S. PATENT DOCUMENTS

| | | |
|---|---|---|
| 4,079,127 | 3/1978 | Goldstein . |
| 4,116,951 | 9/1978 | Wang . |
| 4,148,788 | 4/1979 | Wang . |
| 4,339,427 | 7/1982 | Goldstein et al. . |
| 4,353,821 | 10/1982 | Birr et al. . |
| 4,470,926 | 9/1984 | Birr et al. . |
| 4,504,415 | 3/1985 | Felix et al. . |
| 4,521,407 | 6/1985 | Pelham et al. ............... 424/95 |
| 4,612,365 | 9/1986 | Birr et al. . |
| 4,614,731 | 9/1986 | Horecker . |
| 4,735,896 | 4/1988 | Wang et al. . |
| 4,808,536 | 2/1989 | Chang et al. ................ 435/5 |
| 4,843,011 | 6/1989 | Sarngadharan et al. ....... 435/240.27 |
| 4,863,730 | 9/1989 | Karpas . |

OTHER PUBLICATIONS

Greene, 1993, "AIDS and the Immune System" Scientific American, Sep. 1993, pp. 99–105.
Brown, "AIDS Vaccine Trials Viewed with Caution," 1993, Washington Post Newspaper, Jun. 10, 1993.
"The AIDS Virus", Scientific American, Jan. 1987, pp. 47–56.
"Complete Nucleotide Sequence of the AIDS Virus", HTLV–III, Nature, vol. 313, Jan. 24, 1985, pp. 277–284.
"Nucleotide Sequence of the AIDS Virus, LAV", Cell, vol. 40, Jan. 1985, pp. 9–17.
"Nucleotide Sequence and Expression of an AIDS–Associated Retrovirus" (ARV–2) Science, vol. 227, Feb. 1985, pp. 484–492.
"Will There Be An AIDS Vaccine?", Science News, May 9, 1987, pp. 297–299.
"AIDS Vaccines: The Problems of Human Testing", Science News, May 23, 1987, pp. 329–332.

*Primary Examiner*—Christine M. Nucker
*Assistant Examiner*—Jeffrey Stucker
*Attorney, Agent, or Firm*—Sherman and Shalloway

[57] ABSTRACT

Vaccines effective in the inhibition of infection caused by the family of retroviruses, HTLV–III, Human T-Cell Leukemia Virus, LAV, Lymphadenopathy-associated virus, ARV-2, AIDS-Related Virus, (AIDS and AIDS-Related Complex) have been developed from an antisera prepared against thymosin $\alpha_1$ (T$\alpha_1$), a thymic hormone, as well as from antisera to synthetic peptide fragments of T$\alpha_1$ and antisera to synthetic peptide fragments inclusive of amino acid positions 92–109 of the p17 gag core protein of HTLV–III, LAV and ARV-2. In this 18 amino acid primary sequence there is a 44 to 50% homology between the gag protein and T$\alpha_1$. Immunoglobulin (IgG)-enriched preparations of the T$\alpha_1$ antisera have enhanced activity in blocking viral replication. A diagnostic test capable of directly detecting the presence of HTLV–III, LAV, ARV-2 and related retroviruses associated with AIDS and ARC is also described.

12 Claims, 2 Drawing Sheets

THYMOSIN$\alpha_1$ IMMUNOREACTIVITY IN RETROVIRAL EXTRACTS

SERUM ANTIBODIES TO THE GAG-PEPTIDE OF THE AIDS VIRUS

5,665,536

DIAGNOSTIC METHOD AND TEST KIT FOR THE SEROLOGICAL DETECTION OF THE AIDS VIRUS

This is a division of application Ser. No. 07/884,153, filed May 18, 1992, which is a continuation of application Ser. No. 07/577,672, filed Sep. 5, 1990, now abandoned, which is a division of application Ser. No. 07/300,176, filed Jan. 23, 1989, now U.S. Pat. No. 4,983,387, which is a continuation of application Ser. No. 06/864,599, filed May 19, 1986, now abandoned.

BACKGROUND OF THE INVENTION

1. Field of the Invention

This invention relates to a vaccine for treatment or prevention of Acquired Immune Deficiency Syndrome (AIDS) or pre-AIDS (also known as AIDS-Related Complex or ARC), including novel antibodies and antisera to thymosin $\alpha_1$ peptide fragments and analogs thereof, or to peptide fragments of the p17 gag protein of HTLV-III, LAV, ARV-2 or other similar retrovirus. This invention also relates to the novel peptide fragments and analogs thereof, per se. This invention also relates to a diagnostic test for directly detecting the presence in the blood of the HTLV-III, LAV, ARV-2, etc. retroviruses.

2. Discussion of the Prior Art

Acquired immune deficiency syndrome (AIDS) is a disease which is characterized by a decrease in helper T-cells ($T_4^+$) and $T_4^+/T_8^+$ lymphocyte ratios, an increase in the incidence of opportunistic infections and progressive paralysis of the immune system. The etiologic agent of AIDS has been identified as a human T-lymphotropic retrovirus, HTLV-III (also termed LAV or ARV). In many respects, the clinical symptoms of AIDS are indistinguishable from symptoms often seen in children with rare primary immunodeficiency (PID) diseases associated with thymic aplasia or hypoplasta and an increased susceptibility to opportunistic infections, including pneumocystis carinii pneumonia. The possible involvement of the thymus gland, which plays a key role in the maturation and function of the lymphoid system, in AIDS has been implicated by the detection of elevated levels of a $T\alpha_1$-like peptide in the blood of individuals with AIDS or belonging to the AIDS risk group. See Naylor, P. H. et al, NYAS Monograph on AIDS, 437, 88 (1985); Hirsh, E. M. et al. New Eng. J. Med., 308, 45 (1983); Biggar, R. J. et al. New Eng. J. Med., 309, 49 (1983); Kreiss, J. K. et al, Annal Int. Med, 100, 178 (1984); Kessler, C. M. et al, Brit. J. Hematology, 58, 325 (1984).

$T\alpha_1$ was the first thymic hormone purified to homogeneity and sequenced from the partially purified thymosin fraction 5 (TF 5). See Goldstein, A. L. et al., Proc, Natl. Acad. Sci., USA, 74, 725 (1977) and U.S. Pat. Nos. 4,002,740; 4,010, 148; 4,148,788 and others. It is an acidic polypeptide (pI 4.2) with a molecular weight of 3108, has many of the biological activities of thymosin fraction 5 (TF 5) and is a potent immunomodulator in vivo and in vitro. $T\alpha_1$ acts primarily on helper T-cells and has been found in animals and humans to enhance the expression of T-cell markers and to stimulate the production of a number of lymphokines, including interleukin-2 (IL-2) and γ-interferon, and to restore immune function and tumor immunity. $T\alpha_1$ is currently the first biological response modifier (BRM) which has been shown to restore helper T-cell function and prolong survival in patients with lung cancer following radiotherapy, Schulof, R. S., et al., J. Biol. Resp. Mod. 4, 147 (1985). U.S. Pat. No. 4,521,407 to Pelham, et al. discloses that a particular calf thymus extract can stimulate the cellular immune system of a person having AIDS.

Given the clinical similarities between AIDS and PID's in children, it was expected that $T\alpha_1$ levels would be depressed in patients with AIDS or AIDS Related Complex (ARC). $T\alpha_1$ can be measured by radioimmunoassay as described in U.S. Pat. Nos. 4,264,571 and 4,339,427. Surprisingly, examination of the blood from patients with AIDS and ARC shows markedly elevated levels of $T\alpha_1$. For example, 44 of 72 individuals with Kaposi's sarcoma (60%) and 12 of 22 individuals with *Pneumocystis carinii* pneumonia (54%) had $T\alpha_1$ levels above two standard deviations from the mean of normal individuals. Subsequent studies confirmed the initial findings for a nationwide sampling of patients with AIDS, which included homosexuals and bisexuals, intravenous drug abusers, Haitians, and homosexuals with lymphadenopathy.

Three possible alternatives have been proposed to account for the elevation of $T\alpha_1$: 1) a defect in helper T-cells resulting in increased levels of biologically active peptide, i.e. end-organ failure; 2) a viral invasion of the thymus epithelial cells with subsequent loss of control over hormone production and/or processing; or 3) the presence of a biologically inactive but immunologically cross-reactive protein related to the "AIDS" virus. As reported by Naylor. P. H., et al., AIDS (Alan R. Liss, New York) (1985) (p. 265), further chemical and immunochemical characterization of the $T\alpha_1$-like peptide in the blood of homosexuals at high risk for AIDS indicate that this abnormally elevated peptide may be a cross-reacting molecule and that, in fact, authentic $T\alpha_1$ is often significantly decreased.

In order to identify the $T\alpha_1$ cross-reacting substances, the present inventor initiated a comprehensive search for homologous peptides using computer-assisted analysis. Over 3,500 protein sequences at the sequence bank of the National Biological Research Foundation in Washington, D.C. and the catalogue of available HTLV-III/LAV and other retroviral isolates from the laboratory of Dr. Robert Gallo at the National Cancer Institute (NCI), were used. Although no significant homologous with other thymic hormones or lymphokines were found, it was unexpectedly discovered that $T\alpha_1$ and the gag (core) proteins (p17) of HTLV-III/LAV and ARV-2 share a 44% to 50% homology in an 18 amino acid region (positions 11–28 on $T\alpha_1$ and 92–109 on the p17 gag protein) of their primary sequences.

Currently, essentially all ongoing research strategies for the development of vaccines against diseases induced by HTLV-III/LAV/ARV gene and its products (i.e. proteins and/or glycoproteins), are focussing on the envelope gene, env. See, for example, Fischinger, P. J., et al., "Current Status and Strategies for Vaccines against Diseases Induced by Human T-Cell Lymphotropic Retroviruses (HTLV-I, -II, -III)" Cancer Research, 45 4694s–4699s (Sep. 1985); L. Davis, "AIDS Vaccine Research: Promising Protein", Science News, 129, 10, p.151 (Mar. 8, 1986). Presumably, this strategy is based on the conventional wisdom that the envelope proteins (i.e. outer coat) are most likely to provide the antigenic site(s) which could be "recognized" by the body's immune system leading to the production of antibodies.

However, as pointed out, for example, by Fischinger, et al., due to the extensive heterogeneity and antigenic variations observed among various HTLV-III/LAV isolates in the env gene and corresponding env proteins, development of vaccines with these immunogens is expected to encounter considerable difficulty and may possibly be futile.

3

In contrast, the gag core proteins of HTLV-III/LAV, although not apparently "exposed" to the immune system defenses, are much more highly conserved and greatly less subject to mutation and genetic drift.

The present invention is based on the quite surprising discovery that antigenic determinants common to gag proteins of HTLV-III/LAV are readily accessible to killing with antibodies directed against specific epitopes, namely the apitopes found to have a high degree of homology with thymosin $\alpha_1$.

Robert C. Gallo, et al. in U.S. Pat. No. 4,520,113 describe a diagnostic test for the serological detection of antibodies to HTLV-III in sara of patients with AIDS and ARC conditions. Such diagnostic procedure which is currently in wide practice suffers from various defects leading to false results. Specifically, a diagnostic test which determines the presence of antibodies to HTLV-III/LAV viruses has the following drawbacks which could result in false-negative or false-positive results. Some patients who are exposed to the AIDS virus may have deficient immune responses and not produce any antibodies. Some patients may have been recently exposed but not yet produced any or detectable amounts of antibody (antibodies to AIDS often take up to 8 weeks to be produced in detectable levels). Some patients who have antibodies in their sara may not have any virus remaining in their system. Thus, a "false-positive" result would be given in the latter case while "false-negative" results would be suggested in the two former cases.

Clearly, therefore, a diagnostic test which detects the presence of the AIDS virus directly and selectively would be of extreme importance for the early detection and diagnosis of patients exposed to or in a high risk category for contracting AIDS.

OBJECTS OF THE INVENTION

Accordingly, it is an object of this invention to provide a safe vaccine capable of inducing formation of antibodies which are effective in neutralizing HTLV-III/LAV, ARV or other similar retroviruses associated with Acquired Immune Deficiency Syndrome (AIDS).

A related object is the provision of a method for immunizing individuals at risk for development of AIDS or who have been exposed to the AIDS virus by administering to the individual an immunogenic antigenic material which will elicit the formation of specific neutralizing antibodies capable of blocking the replication of HTLV-III/LAV, ARV and other AIDS viruses.

It is a specific object of the invention to provide such safe vaccine and active immunization method which utilizes as the immunogenic antigenic material thymosin $\alpha_1$ or other novel peptides which share common epitopes with the HTLV-III/LAV/ARV proteins/or utilizing the peptide of the p17 gag protein of the AIDS virus sharing homology with the amino acid sequence at positions 11 to 28 of thymosin $\alpha_1$. or fragments, analogs or polymers of such peptide.

Another object of this invention is to provide antisera capable of blocking replication of HTLV-III/LAV using anti-T$\alpha_1$ serum. IgG-enriched preparations thereof, or antisera to other peptides or analogs that share common epitopes with the gag protein of HTLV-III/LAV or antisera to the core peptide fragments derived from the gag region of the HTLV-III/LAV virus itself.

It is another and related object of the invention to provide novel thymosin $\alpha_1$ peptide fragments and analogs thereof and/or core peptide fragments derived from the gag region of the HTLV-III/LAV virus.

Still another object of this invention is to provide novel immunogens by bonding any of the novel peptides to an immunogenic carrier material.

Still yet another object of this invention is to provide novel antibodies specific to the peptides, fragments and/or epitopes for use in the treatment and prevention of AIDS, and/or AIDS Related Complex (ARC) and the passive immunization against AIDS using such novel antibodies or antisera containing such antibodies, or anti-T$\alpha_1$ antisera, or IgG-enriched preparations thereof.

A further object of the invention is to provide a diagnostic method and kit capable of making a direct serological determination of the presence or absence of the AIDS virus.

These and other objects of the invention which will become apparent by reference to the following detailed discussion and preferred embodiments and with the aid of the accompanying drawings is accomplished, in connection with one aspect thereof, by a method of decreasing viremia associated with Acquired Immune Deficiency Syndrome (AIDS) by administering to an individual exposed to AIDS, at risk for AIDS or infected with AIDS, a natural or synthetic peptide sharing common epitopes with AIDS-associated retrovirus in the amino acid sequence extending from at least about position 92 to about position 109 of the gag region of the core protein of the AIDS-associated retrovirus, thereby inducing the individual to produce antibodies capable of neutralizing the AIDS virus.

Alternatively, the present invention provides a method for inducing passive immunization in a patient suffering from, infected with, or at risk for development of AIDS by administering to the individual a therapeutically effective amount of antibodies to thymosin $\alpha_1$ or to any other peptide sharing common epitopes with AIDS-associated retrovirus in the amino acid sequence extending from at least about position 92 to at least about position 109 of the gag region of the core protein of the AIDS-associated retrovirus, said antibodies being capable of neutralizing the AIDS virus.

Exemplary of the synthetic peptides which can be used as antigen to form antibodies capable of neutralizing the AIDS virus are thymosin $\alpha_1$ peptide fragment or analog thereof having the formula (I)

$$A_o—Ile—X_1—X_2—Lys—Asp—X_3—Lys— \qquad (I)$$
$$Glu—X_4—X_5—X_6—X_7—X_8—Glu—Glu—$$
$$X_9—X_{10}—Asn—OH$$

or a salt, ester, ether or amide thereof, wherein $X_1$-$X_{10}$ are, independently, amino acids, and $A_o$ is H or an amino acid sequence of up to about 6 amino acids, or the peptide fragment of the p17 gag protein of HTLV-III/LAV/ARV, including at least the amino acid sequence 92–109 and having the formula (II)

$$A—Ile—Y_1—Y_2—Lys—Asp—Thr—Lys—Glu—Ala— \qquad (II)$$
$$Leu—Y_3—Lys—Ile—Glu—Glu—Glu—Gln—$$
$$Asn—B$$

where $Y_1$ is Asp or Glu, $Y_2$ is Val or Ile, $Y_3$ is Glu or Asp.

A is H or an amino acid sequence of up to about 10 amino acids, and

B is OH or an amino acid sequence of up to about 10 amino acids, the peptide having a total of no more than about 40 amino acids, preferably up to 36 amino acids, and especially preferably up to about 30 amino acids.

A particularly preferred polypeptide according to this invention is the triacontapeptide fragment of the HTLV-III/

ARV virus at positions 86–115 or the [Ser]^87 analog thereof, having the amino acid sequence represented by the formula Tyr—A₁—Val—His—Gln—Arg—Ile—Asp—Val—Lys—
Asp—Thr—Lys—Glu—Ala—Leu—A₂—Lys—Ile—
Glu—Glu—Glu—Gln—Asn—Lys—Ser—Lys—Lys—Lys—
Ala where $A_1$ is Cys or Ser and $A_2$ is Asp or Glu; and the $^{125}$I-derivative thereof.

DETAILED DESCRIPTION OF THE INVENTION

Figure 1:
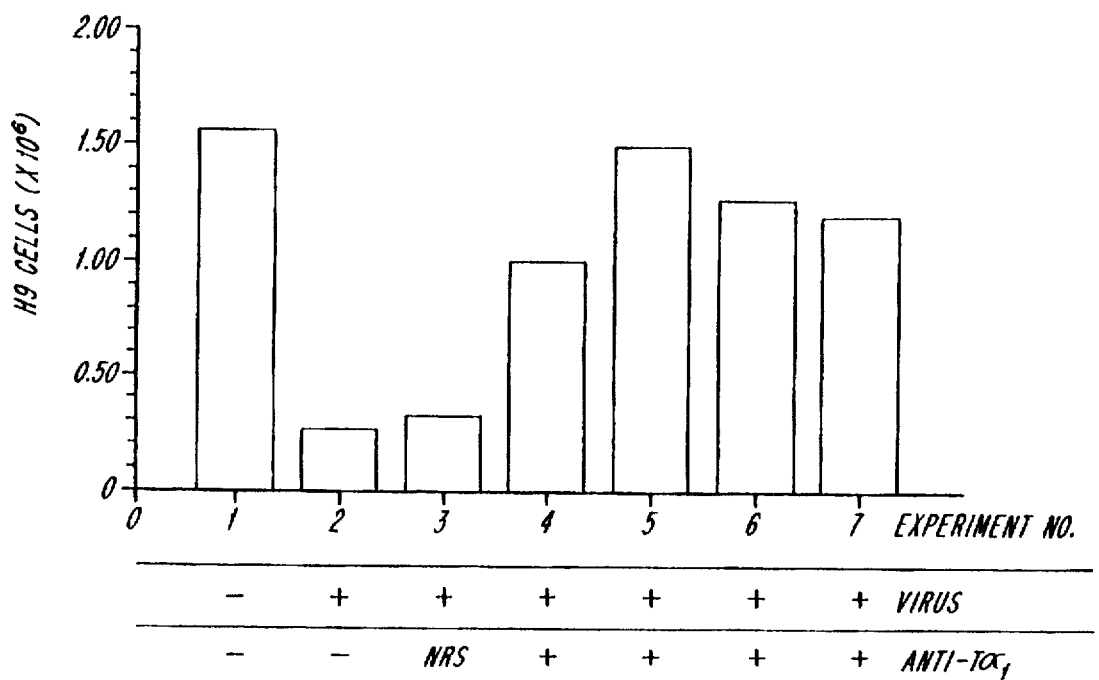
FIG. 1 is a bar graph plotting the ability of antisera to thymosin $\alpha_1$ to inhibit replication of HTLV-III retrovirus in H9 cells, based on the data from table 2.

The family of retroviruses, which are presently known to include the human T-cell lymphotropic and several animal related species, e.g. feline, bovine, rabbit, etc., are characterized by containing a single strand of RNA encased within a protective inner protein coat (core protein) and the encased RNA strand is in turn contained within an outer protein coat (envelope protein). The RNA genome includes a "gag" gene which codes for the core (gag) protein and an env gene which codes for the envelope (env) protein (or glycoprotein). Since the envelope protein is apparently responsible for the mechanism by which the virus attaches itself to the surface of the host cell and is "visible" as the outermost layer of the virus, it is generally expected that the antigenic determinants or epitopes of the virus most likely to be candidates for recognition by the cellular immune system and subject to attack by antibodies are present on the envelope protein. Unfortunately, however, the env gene of HTLV-III/LAV virus exhibits considerable heterogeneity and antigenic variations, and to date no successful vaccine directed against the env protein has been discovered, although extensive research in this area is in progress.

In contrast to the heterogeneity and antigenic variations of the env gene of HTLV-III/LAV, the gag gene, and hence the gag (core) protein appears to be much more conserved. Accordingly, an antibody specific to the core protein would be expected to be effective against a much wider spectrum of the AIDS causing virus.

The present invention has now succeeded in providing antibodies specific to the core protein of HTLV-III/LAV and ARV-2 retroviruses, associated with Acquired Immune Deficiency Syndrome (AIDS). For simplicity, all of the different but related family of retroviruses responsible for AIDS, and AIDS-related complex (ARC) will be collectively referred to herein, and in the appended claims, as AIDS-virus or as Human Immunodeficiency Virus (HIV) which is now the accepted terminology for these retroviruses.

Initially, it was discovered, prompted by the observation of elevated levels of thymosin $\alpha_1$ (T$\alpha_1$) in AIDS patients, that there is a high degree (about 50%) of homology over an 18-amino acid sequence of thymosin $\alpha_1$ and the HTLV-III and ARV viruses. Thymosin $\alpha_1$ has the following amino acid sequence:

Ac—Ser—Asp—Ala—Ala—Val—Asp—Thr—Ser—Ser—Glu—
Ile—Thr—Thr—Lys—Asp—Leu—Lys—Glu—Lys—
Lys—Glu—Val—Val—Glu—Glu—Ala—Glu—Asn—OH

The gag gene of HTLV-III/LAV and ARV-2 encodes for 4 gag proteins containing 512 amino acids, gag p17, gag p24, gag p7 and gag p9, having molecular weights of approximately 17,000, 24,000, 7,000 and 9,000, respectively. Comparison of the primary sequence of thymosin $\alpha_1$, and the p17 gag protein show a 44% to 50% homology in the 18 amino acid region between positions 11 and 28 on thymosin $\alpha_1$ and positions 92 and 109 on the gag protein, as shown below:

| Thymosin $\alpha_1$ | | ARV-2 gag protein | | HTLV-III/LAV gag protein |
|---|---|---|---|---|
| 1 | | 1' | | 1" |
| 11 | Ile | 92' | Ile | 92" Ile |
|  | Thr |  | Asp |  Glu |
|  | Thr |  | Val |  Ile |
| 14 | Lys | 95 | Lys | 95 Lys |
| 15 | Asp | 96 | Asp | 96 Asp |
|  | Leu |  | Thr |  Thr |
| 17 | Lys | 98 | Lys | 98 Lys |
| 18 | Glu | 99 | Glu | 99 Glu |
|  | Lys |  | Ala |  Ala |
|  | Lys |  | Leu |  Leu |
| 21 | Glu | 102 | Glu |  Asp |
|  | Val |  | Lys |  Lys |
|  | Val |  | Ile |  Ile |
| 24 | Glu | 105 | Glu | 105 Glu |
| 25 | Glu | 106 | Glu | 106 Glu |
|  | Ala |  | Glu |  Glu |
|  | Glu |  | Gln |  Gln |
| 28 | Asn | 109 | Asn | 109 Asn |
|  | OH | 512' | OH | 512" OH |

Based on this unusually high degree of homology antibodies to thymosin $\alpha_1$ (AbT$\alpha_1$) were evaluated to detect their ability to neutralize the AIDS virus by measuring their ability to inhibit HTLV-III/LAV replication in the H9 permissive cell line. To detect the presence of neutralizing antibodies to HTLV-III/LAV in the serum of rabbits immunized with thymosin $\alpha_1$, the HTLV-III/LAV replication system in H9 cells as described by P. S. Sarin, et al., *Biochim. Pharmacol.*, 34, 4075 (1985) was used.

Briefly, infection of the H9 cells is monitored by measuring reverse transcriptase (RT) activity in the culture medium and by using an indirect immunofluorescence assay for the expression of p15 and p24 of HTLV-III/LAV. Immunofluorescent assays are done on cells fixed in methanol:acetone (1:1) and with monoclonal antibodies to HTVL-III/LAV p15 and p24. The HTLV-III/LAV infected cells with and without antibody treatment are fixed on toxoplasmosts slides. After fixation with methanol acetone (1:1) for 30 minutes at room temperature, the slides are stored in sealed plastic bags at −20° C. until used. The monoclonal antibodies are added to duplicate wells, incubated at room temperature in a humid chamber for 1 hour and washed with PBS containing 0.25 percent Triton X-100 for 2 hours. The cells are then exposed to fluorescein (FITC) conjugated goat antiserum to mouse IgG (Capell Labs) for 1 hour and washed with PBS buffer containing 0.25% Triton X-100 overnight. The slides are mounted with 50% glycerol and cell fluorescence is observed under a Zeiss fluorescence microscope.

Analyses of ten different lots of heterologous antisera to $T\alpha_1$ prepared in rabbits establish the presence of neutralizing antibodies to HTLV-III/LAV (Table 1). The antisera to $T\alpha_1$ were prepared as described in U.S. Pat. No. 4,264,571 in connection with a radioimmunoassay for thymosin $\alpha_1$. Briefly, synthetic $T\alpha_1$ is coupled via glutaraldehyde to keyhole limpet hemocyanin (KLH) (1:1 by weight) to give a final concentration of $T\alpha_1$ of 100 μg/ml. The conjugate is mixed (1 ml and 1 ml) with Freund's complete adjuvant and-administered to New Zealand white rabbits intradermally in several sites. The rabbits are given booster injections (100 μg of $T\alpha_1$ in Freund's complete adjuvant) at weekly intervals for 6 weeks.(2 to 4 months). After 1 months rest, the animals receive booster injections monthly until maximum titers are achieved. In all cases, RT is significantly inhibited (53±3%), but several of the crude antisera used at a dilution of 1:20 showed some cytotoxicity against the H9 cells and/or failed to inhibit expression of p15 and p24. Accordingly, four lots of $T\alpha_1$ antisera were selected and for each of them an immunoglobulin (IgG)-enriched preparation was prepared to confirm that the antiviral activity is IgG-mediated. The IgG-enriched preparations are prepared by ammonium sulfate (40%) precipitation. After centrifugation, the precipitate is dissolved in PBS and dialyzed for 24 hours against PBS. Each lot is then millipored using an 0.8 micron filter. Instead of, or in addition to ammonium sulfate precipitation, the antisera can be concentrated by other conventional means, such as, for example, staph-A purification, HPLC purification, etc.

As summarized in Table 2, the concentrated IgG preparations of antisera to $T\alpha_1$ are highly effective in neutralizing HTLV-III/LAV; they inhibit the expression of the viral proteins p15 and p24 and the activity of RT and are not cytotoxic against the H9 cells. The antisera from rabbits immunized against $T\alpha_1$ are as effective in neutralizing the AIDS virus as the sera of those patients with ARC and AIDS, which also exhibit neutralizing activity. Thus, not only are antisera or IgG-enriched preparations directed toward the common epitope in $T\alpha_1$ and the gag protein of HTLV-III/LAV highly effective in vitro in neutralizing this virus, but also compare favorably with the anti-neutralizing antibodies present in some sera obtained from patients with AIDS.

TABLE 1

Neutralization of HTLV-III/LAV by whole Antiserum to Thymosin $\alpha_1$

| # | Serum dilution | H9 Cells $10^6$ cells/ml | % of Control p15 | p24 | RT |
|---|---|---|---|---|---|
| Experiment | | | | | |
| 1. H9 cells (no virus) | — | 1.3 | — | — | — |
| 2. H9/HTLV-III/LAV | — | 0.96 | 100 | 100 | 100 |
| 3. #2 + serum from AIS patients Experiments | 1:100 | 1.4 | 25 | 33 | 13 |
| 4. #2 + normal rabbit serum | 1:20 | 1.21 | 100 | 100 | 100 |
| 5. #2 + antiserum to $T\alpha_1$ (Lot 1) | 1:20 | 0.33 | 100 | 33 | 43 |
| 6. #2 + antiserum to $T\alpha_1$ (Lot 2) | 1:20 | 0.33 | 50 | 33 | 42 |
| 7. #2 + antiserum to $T\alpha_1$ (Lot 3) | 1:20 | 0.33 | 50 | 66 | 60 |
| 8. #2 + antiserum to $T\alpha_1$ (Lot 4) | 1:20 | 0.19 | 25 | 33 | 45 |
| 9. #2 + antiserum to $T\alpha_1$ (Lot 5) | 1:20 | 0.14 | 25 | 33 | 59 |

TABLE 1-continued

Neutralization of HTLV-III/LAV by whole Antiserum to Thymosin $\alpha_1$

| # | Serum dilution | H9 Cells $10^6$ cells/ml | % of Control p15 | p24 | RT |
|---|---|---|---|---|---|
| 10. #2 + antiserum to $T\alpha_1$ (Lot 6) | 1:20 | 0.29 | 100 | 133 | 62 |
| 11. #2 + antiserum to $T\alpha_1$ (Lot 7) | 1:20 | 0.71 | 125 | 166 | 72 |
| 12. #2 + antiserum to $T\alpha_1$ (Lot 8) | 1:20 | 0.14 | 125 | 100 | 58 |
| 13. #2 + antiserum to $T\alpha_1$ (Lot 9) | 1:20 | 0.16 | 50 | 33 | 50 |
| 14. #2 + antiserum to $T\alpha_1$ (Lot 10) | 1:20 | 0.31 | 50 | 66 | 42 |

Legend for Table 1
*HTLV-III/LAV infection of H9 cells: H9 cells are treated with polybrene (2 μg/ml) for 30 minutes at 37° C., washed free of polybrene and infected with $2 \times 10^8$ HTLV-III/LAV virus particles per $4 \times 10^5$ H9 cells. For the neutralizing antibody assays, the sera are heat-inactivated at 56° C. for 30 minutes and filtered through 0.45 μm filter. Antibodies at the appropriate dilutions are mixed with HTLV-III/LAV (500 virus particles/cell) in 24-well flat bottom plates (2 ml). The plate is incubated at 4° C. for 1 hour and at 20° C. for 15 minutes. H9 cells are added to the wells to give a final concentration of $5 \times 10^5$ cells/ml. The cultures are incubated at 37° C. and 5% $CO_2$ for 96 hours. After this period, viable cell count is taken in the presence of trypan blue. The cell suspension is centrifuged at 500 xg for 10 minutes. The supernatant is processed for reverse transcriptase assays and the cells are mounted on toxoplasmosis slides, fixed in methanol:acetone (1:1) and analyzed with monoclonal antibodies to HTLV-III/LAV, p15 and p24 as described by P. S. Sarin et al., Biochem. Pharm. 34, 4075 (1985).

TABLE 2

Neutralization of HTLV-III/LAV and Inhibition of Viral Replication with Partially Purified IgG antiserum to Thymosin $\alpha_1$

| # Experiment | Serum Dilutions | H9 Cells $10^6$ cells/ml | % Control RT | p15 | p24 |
|---|---|---|---|---|---|
| 1. H9 cells (no virus) | — | 1.56 | — | — | — |
| 2. H9 + HTLV-III/LAV* | — | 0.26 | 100 | 100 | 100 |
| 3. #2 + normal | 1:20 | 0.32 | 100 | 100 | 100 |
| 4. #2 + antiserum to $T\alpha_1$ (Lot 2**) | 1:20 | 1.00 | 31 | 18 | 21 |
| | 1:50 | 0.98 | 38 | 26 | 36 |
| 5. #2 + Antiserum to $T\alpha_1$ (Lot 5**) | 1:20 | 1.48 | 46 | 21 | 15 |
| | 1:50 | 1.34 | 77 | 58 | 43 |
| 6. #2 + Antiserum to $T\alpha_1$ (Lot 7**) | 1:20 | 1.26 | 36 | 15 | 18 |
| | 1:50 | 1.32 | 62 | 33 | 25 |
| 7. #2 + Antiserum to $T\alpha_1$ (Lot 9**) | 1:20 | 1.18 | 42 | 18 | 18 |
| | 1:50 | 1.02 | 57 | 33 | 28 |

*The H9 cells: H9 cells are treated with polybrene (2 μg/ml) for 30 minutes at 37° C., washed free of polybrene and infected with $2 \times 10^8$ HTLV-III/LAV virus particles per $4 \times 10^5$ H9 cells. The cultures are analyzed on day 4 after infection. Neutralizing antibody assays are carried out as described in Table 1.
**IgG enriched sera is prepared by ammonium sulfate precipitation. Lots of anti-$T\alpha_1$ before purification are tested for activity.

For convenience, the data in Table 2 for H9 cells count is plotted in FIG. 1. It can readily be seen from FIG. 1 that the anti-$T\alpha_1$ antibodies are highly effective in neutralizing the AIDS virus. Furthermore, from this data it is concluded that this epitope region (positions 92 to 109 of the gag protein) of the virus genome is critical to replication of the AIDS virus.

Accordingly, the present invention provides an antisera for prevention or treatment of AIDS which in one embodiment thereof is based on the administration of antibodies to thymosin $\alpha_1$ or antibodies to peptide fragment or analogs of thymosin $\alpha_1$, inclusive of at least the common epitope region at positions 11 to 28, or antibodies to the common epitope of the p17 gag core protein of HTLV-III/LAV or ARV-2, inclusive of at least from about position 92 to at least about position 109 (i.e. passive immunization). In an alternative embodiment (active immunization) any of these peptides provide a vaccine which when administered to an individual exposed to the AIDS virus, at risk for AIDS, or infected by AIDS will induce the individual's immune system to produce antibodies which are specific to the peptide and which is effective in inhibiting replication of the AIDS virus.

Those peptide fragments at the C-terminus of thymosin $\alpha_1$ and the analogs thereof which are represented by the following formula (I):

$$A_o-Ile-X_1-X_2-Lys-Asp-X_3-Lys-Glu-X_4-X_5-X_6-X_7-X_8-Glu-Glu-X_9-X_{10}-Asn-OH \quad (I)$$

or the salt, ester, ether, or amide thereof, wherein $A_o$ is H or an amino acid sequence of from 1 to about 6 amino acids, and $X_1-X_{10}$ are, independently, any of the naturally occuring amino acids; and the peptide fragments of the antigenic region at at least positions from about 92 to about 109 of the gag core protein, which are represented by the following formula (II):

$$A-Ile-Y_1-Y_2-Lys-Asp-Thr-Lys-Glu-Ala-Leu-Y_3-Lys-Ile-Glu-Glu-Glu-Gln-Asn-B \quad (II)$$

where $Y_1$ is Asp or Glu, $Y_2$ is Val or Ile, $Y_3$ is Glu or Asp,

A is H or an amino acid sequence of up to about 10 amino acids, and

B is OH or an amino acid sequence of up to about 10 amino acids, the peptide having no more than about 40 amino acids, in total, are themselves novel compositions of matter and the antibodies to the peptides of formulas (I) and (II) are also novel compositions of matter, as are the antisera and vaccines containing these antibodies or peptides.

In the peptides of formula (I) the X's ($X_1-X_{10}$) may be any of the naturally occurring amino acids, namely alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophane (Trp), tyrosine (Tyr) and valine (Val). Similarly, when $A_o$ represents one or more amino acids it may comprise any of these amino acids in any arbitrary combination, or $A_o$ may be an amino acid sequence adjacent to Ile on the N-terminal end of thymosin $\alpha_1$, i.e. Glu, Ser-Glu, Ser-Ser-Glu, Thr-Ser-Ser-Glu, Asp-Thr-Ser-Ser-Glu, Val-Asp-Thr-Ser-Ser-Glu, and so on.

When $X_1$ is Thr, $X_2$ is Thr, $X_3$ is Leu, $X_4$ is Lys, $X_5$ is Lys, $X_6$ is Glu, $X_7$ is Val, $X_8$ is Val, $X_9$ is Ala and $X_{10}$ is Glu, the peptide of formula (I) corresponds to the $C_{11-28}$ terminal of thymosin $\alpha_1$ and has the formula (I)-1:

$$A_o-Ile-Thr-Thr-Lys-Asp-Leu-Lys-Glu-Lys-Lys-Glu-Val-Val-Glu-Glu-Ala-Gln-Asn-OH \quad (I)-1$$

In formula (I) it is especially preferred that $X_6$ is Glu or Asp, the former corresponding to the Glu at position 102 of ARV-2 and the latter corresponding to Asp at position 102 of HTLV-III/LAV.

Since the anti-T$\alpha_1$ antiserum is effective in neutralizing the AIDS virus it is probable that the amino acids $X_1-X_{10}$, particularly $X_1-X_5$ and $X_7-X_{10}$ are less critical to antibody recognition.

On the other hand, in the peptide of formula (I) when $X_1$ is Asp, $X_2$ is Val, $X_3$ is Thr, $X_4$ is Ala, $X_5$ is Leu, $X_6$ is Glu, $X_7$ is Lys, $X_8$ is Ile, $X_9$ is Glu and $X_{10}$ is Gln, then the resulting peptide of formula (I)-2

$$A_o-Ile-Asp-Val-Lys-Asp-Thr-Lys-Glu-Ala-Leu-Glu-Lys-Ile-Glu-Glu-Glu-Gln-Asn-OH \quad (I)-2$$

corresponds identically to the ARV-2gag protein at positions 92 to 109. i.e. 100% homology and should provide even more highly effective antibodies to the AIDS virus.

Similarly, when $X_1$ is Glu, $X_2$ is Ile, $X_3$ is Thr, $X_4$ is Ala, $X_5$ is Leu, $X_6$ is Asp, $X_7$ is Lys, $X_8$ is Ile, $X_9$ is Glu, and $X_{10}$ is Gln, the resulting peptide of formula (I)-3

$$A_o-Ile-Glu-Ile-Lys-Asp-Thr-Lys-Glu-Ala-Leu-Asp-Lys-Ile-Glu-Glu-Glu-Gln-Asn-OH \quad (I)-3$$

corresponds identically to the HTLV-III/LAV gag protein at positions 92 and 109 and also provides an especially effective antibody to the AIDS virus.

Still further, while it is apparent that the antigen of the core protein of the AIDS virus at positions 92 to 109 is critical in the viral replication process, it is also convenient to extend the polypeptide chain length at either end or both ends of the amino acid sequence to include an arbitrary amino acid sequence of from 1 to 10 amino acids, preferably 1 to 8 amino acids, and especially preferably 1 to 6 amino acids, to provide polypeptides having from 18 to 40 amino acids, preferably 18 to 36 amino acids, and especially preferably 18 to 30 amino acids. However, rather than arbitrary amino acid sequences, it is especially preferred to add to either or both ends of the peptide of formula (II) amino acid sequences (joined, of course, by peptide bonds—the same applying above) corresponding to the sequence present in the AIDS virus.

Accordingly, in a particularly preferred embodiment of the invention, there is provided an octadeca- to triacontapeptide fragment of the p-17 gag protein of HTLV-III/LAV, ARV-2, or similar AIDS retrovirus including the amino acid sequence 92 to 109 and the des-87 analogue thereof and having the formula (II)-1:

$$A^1-Ile-Y_1-Y_2-Lys-Asp-Thr-Lys-Glu-Ala-Leu-Y_3-Lys-Ile-Glu-Glu-Glu-Gln-Asn-B^1 \quad (II)-1$$

where $Y_1$, $Y_2$, and $Y_3$ are as defined above for formula (II) and $A^1$ is a member selected from the group consisting of

H

Arg,

Gln-Arg,

His-Gln-Arg,

Val-His-Gln-Arg,

Ser-Val-His-Gln-Arg,

Cys-Val-His-Gln-Arg,
Tyr-Ser-Val-His-Gln-Arg,
Tyr-Cys-Val-His-Gln-Arg,
and B¹ is a member selected from the group consisting of
OH,
Lys,
Lys-Ser,
Lys-Ser-Lys,
Lys-Ser-Lys-Lys
Lys-Ser-Lys-Lys-Lys,
Lys-Ser-Lys-Lys-Lys-Ala The peptides of the present invention represented by the general formula (I) and (II) can be prepared by convention processes for synthesizing peptides; more specifically, using processes as described in Schroder and Lubke, *The Peptides*, Vol. 1 (1966), published by Academic Press, New York, U.S.A., or Izumiya et al., *Synthesis of Peptides*, (1975), published by Maruzen Publishing Co., Ltd., for example, an azide process, a chloride process, an acid anhydride process, a mixed anhydride process, a DCC process, an active ester process (a p-nitrophenyl ester process, an N-hydroxysuccinimide ester process, a cyanomethyl ester process, etc.), a process using a Woodward reagent K, a carbodiimidazole process, an oxidation reduction process, a DCC/additive (HONB, HOBt, HOSu) process, etc. Solid phase and liquid phase synthesis are both applicable to the foregoing processes.

The peptides of the present invention are prepared in accordance with the aforesaid processes for synthesizing ordinary polypeptides, generally either by a so-called stepwise process which comprises condensing an amino acid to the terminal amino acid one by one in sequence, or by coupling fragments divided into several groups to the terminal amino acid. In more detail, for example, in case that a solid phase synthesis is adopted, the C terminal amino acid is bound to an insoluble carrier through its carboxyl group. The insoluble carrier is not particularly limited as long as it has a binding capability to a reactive carboxyl group and is inert to the reagents and reaction conditions of the stepwise condensation-deprotection reactions. Examples of such insoluble carriers include halogenomethyl resins such as chloromethyl resin, particularly chloromethyl-polystyrene-divinylbenzene polymer, bromomethyl resin, etc, hydroxymethyl resins, phenol resins, tert-alkyloxy-carbonylhydrazidated resins, crosslinked poly-N-acrylyl-pyrrolidine resins, etc. In case of, for example, the polypeptides of formulas (I), (I)-1, (I)-2 or (I)-3 wherein the C-terminal amino acid has an amide functional group, as in asparagine (Asn),

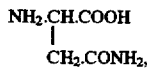

it is convenient to use a benzhydrylamine resin support, whereby the amide functional group can be directly formed on the resin support. Furthermore, according to a particularly preferred embodiment, the solid phase synthesis process for producing the peptides of formulas (I) and any other peptides in which the C-terminal amino acid includes an amide functional group, is carried out using methylbenzhydrylamine resin support as described in greater detail in the commonly assigned copending application of Su-Sun Wang, Ser. No. 849,835, filed Apr. 8, 1986, now U.S. Pat. No. 4,855,407, the disclosure of which is incorporated herein in its entirety by reference thereto.

After the amino protective group is removed, an amino group-protected amino acid is bound in sequence in accordance with the desired amino acid sequence as shown, for example, by general formula (I), through condensation of its reactive amino group and the reactive carboxyl group, in sequence, to synthesize step by step. After synthesizing the complete sequence, the peptide is split off from the insoluble carrier to produce the protein, using, for example, HF, HBr, or other cleavage agent.

In the description above and following, the abbreviations have the following meaning according to standard customary nomenclature:

Boc, t-butyloxycarbonyl, Bzl, benzyl; DCC, dicyclohexylcarbodiimide; Cbz, benzyloxycarbonyl; TFA, trifluoroacetic acid, and ClZ, 2-chlorobenzyloxycarbonyl.

While specific protecting groups are described below, it is within the skill of the art to utilize equivalent conventional protecting groups. The practitioner will readily recognize that certain general conditions will preferably be selected regardless of the particular peptide being synthesized. For example, it is well recognized that the α-amino group of each amino acid employed in the peptide synthesis must be protected during the coupling reaction to prevent side reactions involving the reactive α-amino function. Similarly, for those amino acids containing reactive side-chain functional groups (e.g. sulfhydryl, α-amino, hydroxyl, carboxyl), such functional groups need also be protected both during the initial coupling of the amino acid containing the side-chain group and during the coupling of subsequent amino acids. Suitable protecting groups are known in the art. [See, for example, *Protective Groups in Organic Chemistry*, M. McOmie, Editor, Plenum Press, N.Y., 1973.]

In selecting a particular protecting group, the following conditions must be observed: an α-amino protecting group must: (1) be stable and render the α-amino function inert under the conditions employed in the coupling reaction, and (2) must be readily removable after the coupling reaction under conditions that will not remove the side chain protecting groups or alter the structure of the peptide fragment. A side chain protecting group must: (1) be stable and render the side chain functional group inert under the conditions employed in the coupling reaction, (2) be stable under the conditions employed in removing the α-amino protecting group and (3) be readily removable upon completion of the desired amino acid sequence under reaction conditions that will not alter the structure of the peptide chain, or racemization of any of the central centers contained therein. Suitable protecting groups for the α-amino function are t-butyloxycarbonyl (Boc), benzyloxycarbonyl (Cbz), biphenylisopropyloxycarbonyl, t-amyloxycarbonyl, isobornyloxycarbonyl, 1,1-dimethyl-2,5-dimethoxybenzyloxycarbonyl, o-nitrophenylsulfenyl, 2-cyano-t-butyloxycarbonyl, 9-fluorenylmethyloxycarbonyl and the like, especially t-butyloxycarbonyl (Boc).

As examples of carboxyl-protecting groups, there may be mentioned such ester-forming groups as those capable of giving alkyl ester (e.g. methyl, ethyl, propyl, butyl, t-butyl, etc., esters), benzyl ester, p-nitrobenzyl ester, p-methoxybenzyl ester, p-chlorobenzyl ester, benzhydryl ester, etc. and hydrazide-forming groups such as those capable of giving carbobenzoxy hydrazide, t-butyloxycarbonyl hydrazide, trityl hydrazide, etc.

As groups for protecting the guanidino group of arginine, there may be mentioned nitro, tosyl (Tos), p-methoxybenzene-sulfonyl, carbobenzoxy, isobornyloxycarbonyl, admantyloxycarbonyl, etc. The guanidino group may also be protected in the form of a salt with an acid (e.g. benzenesulfonic acid, toluenesulfonic acid, hydrochloric acid, sulfuric acid, etc.).

The hydroxyl group of threonine may be protected, for example, by way of known estertfication or estertfication. As examples of groups suitable for said esterification, there may be mentioned lower alkanoyl groups (e.g. acetyl), aroyl groups (e.g. benzoyl), and groups derived from carbonic acid, such as benzyloxycarbonyl, ethyloxycarbonyl, etc. As groups suitable for said estertfication, there may be mentioned benzyl, tetrahydropyranyl, t-butyl, etc. The hydroxyl group of threonine, however, need not necessarily be protected. Methionine may be protected in the form of a sulfoxide. Other preferred side chain protective groups for particular amino acids include; for tyrosine: benzyl, o-bromobenzyloxycarbonyl (BrZ), 2,6-dichlorobenzyl, isopropyl, cyclohexyl, cyclopentyl and acetyl; for histidine: benzyl, benzyloxycarbonyl, p-toluenesulfonyl, trityl and 2,4-dinitrophenyl; for tryptophan: formyl.

As typical procedures for the initial coupling of the C-terminal amino acid to the solid resin support the following guidelines are mentioned. For benzhydrylamine or methylbenzhydrylamine resin, the $N^\alpha$-Boc-amino acid or similarly protected C-terminal amino acid is attached to the (methyl)benzhydrylamine resin by means of an N,N'-dicyclohexylcarbodiimide (DCC)/1-hydroxybenzotriazole (HBT) mediated coupling for from about 2 to 24 hours, preferably about 12 hours at a temperature of between about 10° and 50° C., preferably 25° C., in a solvent such as dichloromethane or DMF, preferably dichloromethane. For chloromethyl polystyrenedivinylbenzene type of resin: The attachment to the resin is made by means of the reaction of the $N^\alpha$-protected amino acid, especially the Boc-amino acid, as its cesium, tetramethylammonium, triethylammonium, 4,5-diazabtcyclo-[5.4.0]-undec-5-ene, or similar salt in ethanol, acetontrile, N,N-dimethylformamide (DMF), and the like, especially the cesium salt in DMF, with the chloromethyl resin at an elevated temperature, for example, between about 40° to 60° C., preferably about 50° C., for from about 12 to 48 hours, preferably about 24 hours.

The removal of the $N^\alpha$-protecting groups may be performed in the presence of, for example, a solution of trifluoroacetic acid in methylene chloride, hydrogen chloride in dioxane, hydrogen chloride in acetic acid, or other strong acid solution, preferably 50% trifluoroacetic acid in dichloromethane at about ambient temperature. The coupling of successive protected amino acids can be carried out in an automatic polypeptide synthesizer, as well known in the art. Each protected amino acid is preferably introduced in approximately 2.5 or more molar excess and the coupling may be carried out in dichloromethane, dichloromethane/DMF mixtures, DMF and the like, especially in methylene chloride at about ambient temperature. Other solvents which are known to be useful for the purpose of peptide-forming condensation reaction, for example, dimethylsulfoxide, pyridine, chloroform, dioxane, tetrahydrofuran, ethyl acetate, N-methylpyrrolidone, etc., as well as suitable mixtures thereof, may also be used.

The reaction temperature for the condensation/coupling reaction may be selected from the range known to be useful for the purpose of peptide-forming condensation reactions. Thus, it may normally be within the range of about −40° C. to about 60° C., and preferably, about −20° C. to about 0° C. The coupling agent is normally DCC in dichloromethane but may be N,N'-di-iso-propylcarbodiimide or other carbodiimide either alone or in the presence of HBT, N-hydroxysuccinimide, ethyl 2-hydroxyimino-2-cyanoacetate, other N-hydroxyimides or oximes. Alternatively, protected amino acid active esters (e.g. p-nitrophenyl, pentafluorophenyl and the like) or symmetrical anhydrides may be used.

The coupling, deprotection/cleavage reactions and preparation of derivatives of the polypeptides are suitably carried out at temperatures between about −10° and +50° C., most preferably about 20°–25° C. The exact temperature for any particular reaction will, of course, be dependent upon the substrates, reagents, solvents and so forth, all being well within the skill of the practitioner. The fully deprotected polypeptide may then be purified by a sequence of chromatographic steps employing any or all of the following types: ion exchange on a weakly basic resin in the acetate form; gel permeation chromatography, e.g. on Sephadex G-25; hydrophobic adsorption chromatography on undertvatized polystyrene-divtnylbenzene (for example, Amberlite XAD); silica gel adsorption chromatography; ion exchange chromatography, e.g. on Sephadex G-25, or countercurrent distribution; high performance liquid chromatography (HPLC), especially reverse phase HPLC on octyl- or octadecylsilyl-silica bonded phase column packing.

Although the synthetic peptides according to this invention can be prepared by the above-described chemical preparations, especially the solid phase peptide synthesis, described above, with high efficiency, it is also within the scope of the invention to produce the novel thymosin peptide fragments or analogs of formula (I) or the gag protein fragments of analogs thereof of formula (II), by genetic engineering technology, as is now well known in the art. Thus, using appropriate enzymes and microorganisms (e.g. bacteria, such as *E. coli*) the DNA sequence encoding for the desired polypeptide can be incorporated into the genome of the microorganism, thereby causing the microorganism to express the particular peptide of interest.

Once the particular peptide is obtained and purified, it may be used as a hapten to prepare an antigenic immunogen and from the antigen, antibodies having specific cross-reactivity with the gag core protein of HTLV-III/LAV, ARV-2 and similar AIDS viruses, and having neutralizing capability for the AIDS virus can readily be obtained in large amounts and stably. The specific antibodies can, therefore, be used in a similar manner as described above for the antibody to thymosin $\alpha_1$, namely as antisera for inhibiting replication of the AIDS virus. The antibodies can be used for purification of/HTLV-III/LAV, ARV-2, etc., by binding these antibodies to carriers for use in, e.g. affinity chromatography, and utilizing the bound antibodies in the affinity chromatography. The specific antibodies can also be used as specific antibodies in various immunological measurements of HTLV-III/LAV, ARV-2, and so on. Therefore, the antibodies according to this invention are valuable for directly diagnosing, with high specificity, the presence in blood sera of the AIDS virus.

Polypeptides displaying the antigenicity of the p17 gag protein and antibodies raised with them can be employed in these diagnostic methods to detect the presence of, respectively, antibodies to the AIDS virus or the AIDS virus, per se. These polypeptides and their antibodies may be packaged in diagnostic kits either alone or in combination with any or all of the other HTLV-III/LAV, ARV, etc. antigens and antibodies. These methods and kits, using polypeptides or antibodies of this invention either alone or in combination with other antigens or antibodies, will allow the rapid and convenient identification of AIDS infective carriers and prediction of the course of ARC and AIDS disease. Brief descriptions of typical radioimmunoassay and ELISA for detecting AIDS virus are given below.

Radioimmunoassay to detect AIDS virus: Antibodies to thymosin $\alpha_1$, antibodies to peptide fragments of or analogs of thymosin $\alpha_1$ Inclusive of at least the amino acids isoleucine, lysine, aspartate, lysine, glutamate, glutamate, glutamate and asparagine at positions 11, 14, 15, 17, 18, 24, 25 and 28, respectively, of thymosin $\alpha_1$ or antibodies to the antigenic determinant of the amino acid sequence at least positions 92 to 109 of the p17 gag protein of the AIDS virus produced as above are attached to a solid phase, for example, the inside of a test tube. A sample of the patient's serum is added to a tube, together with a known amount of polypeptides displaying the antigenicity of p17 gag protein of the AIDS virus produced as above and labelled with a radioactive isotope such as radioactive iodine. Any AIDS virus (with associated gag proteins) in the patient's serum will compete with the labelled polypeptides displaying the antigenicity of the p17 gag protein of the AIDS virus for binding with the bound antibodies. The excess liquid is removed, the test tube washed, and the amount of radioactivity measured. A positive result, i.e. that the patient's serum contains AIDS virus, is indicated by a low radioactive count left in the tube. Instead of the solid phase RIA as described above it may be more convenient in some cases to perform liquid phase RIA. In the case of liquid phase RIA the antibodies recognizing the AIDS virus, e.g. anti-T$\alpha_1$, are not attached to a solid phase, but are allowed to react in the liquid phase with the patient's serum in competition with the labelled antigenic material. The antibody-antigen interaction complex can then be detected by any suitable means. For example, a second antibody reactive to the first antibody (such as an antiantibody raised to the first antibody but in a different animal) bound to an insoluble bead can be used to withdraw the complex from the liquid phase.

ELISA to detect AIDS virus: a microtiter plate is coated with antibodies to thymosin $\alpha_1$, or to a peptide of formula (I) or to a peptide of formula (II) displaying the antigenicity at position 91 to 109 of the p17 gag protein of the AIDS virus prepared in accordance with this invention, and to this is added a sample of patient's serum. After a period of incubation permitting interaction of any p17 gag protein of AIDS virus present in the serum with the bound antibodies, the plate is washed. A preparation of antibodies directed to AIDS virus, which can be the same antibody as on the plate (e.g. a so-called "sandwich"), linked to an enzyme, is added. Incubation allows an antibody-antigen reaction to take place, and the plate is then rewashed. Thereafter, enzyme substrate is added to the microtiter plate and incubated for a period of time to allow the enzyme to work on the substrate, and the absorbance of the final preparation is measured. A large change in absorbance indicates a positive result.

The details of the radioimmunoassay and ELISA outlined above demonstrate that the production of polypeptides displaying the antigenicity of p17 gag protein of AIDS virus by the processes of this invention allow AIDS virus and antibodies to AIDS virus to be detected by the standard techniques already routinely employed in medical facilities and research laboratories.

The peptides of the present invention are utilizable as labelled antigens employed in radioimmunoassay (RIA) or enzyme immunoassay (EIA), particularly enzyme linked immunosorbent assay (ELISA), by introducing thereto radioactive substances such as $^{125}$I, $^{131}$I, $^{3}$H (tritium), $^{14}$C, etc.; various enzyme reagents such as peroxidase (POX), chymotripsinogen, procarboxypeptidase, glyceraldehyde-3-phosphate dehydrogenase, amylase, phosphorylase, D-Nase, P-Nase, β-galactosidase, glucose-6-phosphate dehydrogenase, ornithine decarboxylase, etc. The introduction of the above radioactive substance can be effected in a conventional manner. For example, the introduction of radioactive iodine, $^{125}$I, can be carried out by the oxidative ionization method using chloramine T (W. M. Hunter and F. C. Greenwood, Nature, 194, 495 (1962), Biochem. J., 89, 144 (1963), or by using the Bolten-Hunter reagent ($^{125}$I-iodinated p-hydroxyphenyl propionic acid N-hydroxysuccinimide ester) as described in Biochem. J., 133, 529 (1973). See Example 2 in U.S. Pat. No. 4,264,571, etc.

More particularly, this method can be carried out in an appropriate solvent, e.g. 0.2M phosphate buffer solution (pH 7.4) in the presence of chloramin T at about room temperature for about 10 to 30 seconds. The peptide, radioactive iodine 125 and chloramine T are used in ratios of about 1 mCi of the radioactive iodine per nmol of tyrosine contained in the peptide and 10 to 100 nmol of chloramin T per nmol of tyrosine contained in the peptide when introducing one atom of the radioactive iodine per molecule of tyrosine, and about 2 mCi of the radioactive iodine per nmol of tyrosine contained in the peptide of 10 to 100 nmol of chloramin T per nmol of tyrosine contained in the peptide when introducing two atoms of the radioactive iodine per molecule of tyrosine. The thus prepared radioactive iodine labelled peptides can be isolated and purified from the reaction mixture by a conventional separation techniques e.g. extraction, distribution, column chromatography, dialysis, etc. The thus obtained peptides can be stored after freeze drying, if desired.

Or, for the peptides of formula (II)-1 wherein $A^1$ is Tyr-Cys-Val-His-Gln-Arg or Tyr-Ser-Val-His-Gln-Arg the $^{125}$I can be directly incorporated into the N-terminal Tyr, such as by, for example, the procedure described in Example 3b of U.S. Pat. No. 4,339,427.

The introduction of enzyme reagents can be conducted by known methods such as conventional coupling reactions, e.g. the B. F. Erlanger, et al method (*Acta Endoerinol. Suppl.*, 168, 206 (1972)), the M. H. Karol et al. method (*Proc. Natl. Acd. Sci. U.S.A.*, 57 713 (1967)), etc. That is, a peptide and an enzyme are reacted in a buffer solution having a pH of 4 to 6, e.g. 1 mM acetate buffer (pH 4.4) in the presence of an oxidizing agent such as NaIO$_4$ at about room temperature for 2 to 5 hours, followed by reduction with NaBH$_4$ or the like. The enzyme can be used in an amount of 1 to 3 mols per mole of the peptide. It is preferred that the oxidizing agent be used in an amount of about 100 to about 300 mols per mol of the peptide and the reducing agent be used in an amount of about 1 to about 2 mols per mol of the oxidizing agent. The thus obtained enzyme-labelled peptide can be isolated, purified and stored in a manner similar to the processes used in the case of the radioactive iodine-labelled peptide.

It is recognized in the art that polypeptides, i.e. peptides containing less than about 50 amino acids, will not generally directly elicit production of a corresponding antibody. For this reason, it is the usual practice to couple or conjugate the polypeptide antigen, as a hapten, to a hapten-carrier, hereinafter referred to as "immunogenic carrier material" to thereby elicit the production of specific antibodies in sufficiently high titers to be easily recoverable. Nevertheless, it is also known that certain polypeptide antigens, inclusive of certain HTLV-III/LAV env peptides are very strongly immunogenic and can directly induce the immune system to produce specific antibodies. (Unfortunately, to date, none of such anti-env antibodies have been capable of neutralizing the AIDS virus, presumably because the particular antigens of the env protein are not required for vital replication.) In the present invention while it is generally preferred to use the thymosin $\alpha_1$ or gag peptides (including fragments and analogs) as haptens, coupled to an immunogenic carrier material, it is also within the scope of the invention, particularly for the peptides with at least about 26 amino acids, to directly use the peptides as vaccines or as immunogenic antigens in the production of specific antibodies, as well as, of course, in the diagnostic aspects of the invention. Still further, it is within the scope of the invention to utilize any of the novel peptides of formula (I) or formula (II) in the form of its polymer, such as dimer, trimer or oligomer, that is as repeating sequences containing the amino acids of the synthetic peptide. Thus, the synthetic peptides can be polymerized to build up a chain of two or more repeating units so that repeating sequences serve both as "carrier" and immunologically active site.

Hereafter processes for production of immunogenic antigens using the peptides of the present invention as haptens will be described in detail.

The aforesaid antigens are prepared by using the peptides of the present invention as haptens and reacting the peptides with a suitable immunogenic carrier material in the presence of a hapten-carrier binding agent. In this case, natural and synthetic proteins having a high molecular weight which are conventionally employed in the preparation of antigens can be widely employed as carriers to be bound to haptens. In addition, smaller peptides or molecules, such as tufsin (a tetrapeptide), analogs of tufsin, and muramyl dipeptides, and their analogs can act equally well as "immunogenic carrier materials."

As used herein the term "immunogenic carrier material" is meant to include those materials which have the property of independently eliciting an immunogenic response in a host animal and which can be covalently coupled to polypeptide either directly via a formation of peptide or ester bonds between free carboxyl, amino or hydroxyl groups in the polypeptide and corresponding groups on the immunogenic carrier material or alternatively by bonding through a conventional bifunctional linking group. Examples of such carriers include albumins of animal sera such as horse serum albumin, bovine serum albumin, rabbit serum albumin, human serum albumin, sheep serum albumin, etc.; globulins of animal sera such as horse serum globulin, bovine serum globulin, rabbit serum globulin, human serum globulin, sheep serum globulin, etc.; thyroglobulins of animals such as horse thyroglobulin, bovine thyroglobulin, rabbit thyroglobulin, human thyroglobulin, sheep thyroglobulin, etc.; hemoglobulins of animals such as horse hemoglobulin, bovine hemoglobulin, rabbit hemoglobulin, human hemoglobulin, sheep hemoglobulin, etc.; hemocyanins of animals such as Keyhole limpet hemocyanin (KLH), etc.; proteins extracted from ascaris (ascaris extracts, such as those described in Japanese Patent Application (OPI) No. 16,414/81, J. Immun., 111, 260–268 (1973), ibid., 122, 302–308 (1979), ibid., 98, 893–900 (1967) and Am. J. Physiol., 199, 575–578 (1960), or purified products thereof); polylysine, polyglutamic acid, lysine-glutamic acid coplymers, copolymers containing lysine or ornithine, etc. Recently, vaccines have been produced using diphtheria toxoid or tetanus toxoid as immunogenic carrier materials (see Lepow. M. L., et al., J. of Infectious Diseases, Vol. 150, No. 3, page 402–406 (1984); and Coen Beuvery, E., et al., Infection and Immunity 40, pages 39–45 (April 1983) and these toxoid materials can also be used herein. Other suitable carriers are disclosed in, for example, U.S. Pat. No. 4,575, 495, including vaccines, organic polymers, etc.

As hapten-carrier binding agents, those conventionally employed in the preparation of antigens can be widely employed. Specific examples of these agents include diazonium compounds for crosslinking tyrosine, histidine, tryptophane, etc., e.g. bisdiazotized benzidine (BDB), etc.; aliphatic dialdehydes for crosslinking an amino group with an amino group, e.g. $C_2$–$C_7$ alkanals, such as glyoxal, malonedialdehyde, glutaraldehyde, succinaldehyde, adipaldehyde, etc.; dimaletmtde compounds for crosslinking a thiol group with a thiol group, e.g. N,N'-o-phenylenedimaleimide, N,N'-m-phenylenedimaleimide, etc.; maleimidocarboxyl-N-hydroxysuccinimide esters for crosslinking an amino group with a thiol group, e.g. metamaleimidobenzoyl-N-hydroxysuccinimide ester, 4-(maleimidomethyl)-cyclohexane-1-carboxyl-N'-hydroxysuccinimide ester, etc.; agents used in conventional peptide bond forming reactions in which amide bonds are formed from an amino group and a carboxyl group, e.g. dehydrating and condensing agents such as carbodiimides, e.g. N,N-dicylohexylcarbodiimide, N-ethyl-N'-dimethylaminocarbodiimide, 1-ethyl-3-diisopropylaminocarbodiimide, 1-cyclohexyl-3-(2-morpholinyl-4-ethyl)carbodimide, etc. As the foregoing hapten-carrier binding agent, It is also possible to use diazonium aryl carboxylic acids such as p-diazonium phenylacetic acid, etc., with conventional peptide bond forming agents such as the dehydrating and condensing agents described above in combination.

The covalent coupling of thymosin $\alpha_1$ or its peptide fragment or analog thereof to the immunogenic carrier material can be carried out in a manner well known in the art. Thus, for example, for direct covalent coupling it is possible to utilize a carbodiimide, most preferably dicyclohexylcarbodiimide or 1-ethyl-3-(3-dimethylaminopropyl) carbodiimide as coupling agent. In such direct coupling it is desirable to utilize a slightly acidic reaction medium for this step, e.g. a medium having a pH in the range of from about 3 to 6.5, most preferably in the range of from about 4 to 6.5.

The coupling reaction for preparing antigens using as haptens those peptides of formula (I) or formula (II) which are neutral or alkaline can be carried out in similar manner but in an aqueous solution or coventional buffer solution having pH of 7 to 10, preferably in a buffer solution having pH of 8 to 9, at temperatures of about 0° to 40° C., preferably around room temperature. The reaction is generally completed within about 1 to about 24 hours, preferably 3 to 5 hours. Representative examples of buffer solutions which can be used in the above process include:

0.2M sodium hydroxide-0.2M boric acid-0.2M potassium chloride buffer solution;

0.2M sodium carbonate-0.2M boric acid-0.2M potassium chloride buffer solution;

0.05M sodium tetraborate-0.2M boric acid-0.05M sodium chloride buffer solution;

0.1M dihydrogen potassium phosphate-0.05M sodium tetraborate buffer solution.

In the above, proportions of the hapten, hapten-carrier binding agent and carrier can be appropriately determined but it is preferred that the carrier be employed in an amount of about 1 to about 6 times, preferably about 1 to about 5 times the weight of the hapten and the hapten-carrier binding agent be employed in an amount of about 5 to about 10 times the mol of the hapten. By the above reaction, the carrier is bound to the hapten via the hapten-carrier binding agent to obtain a desired antigen composed of a peptide-carrier complex.

After completion of the reaction, the thus obtained antigen can easily be isolated and purified by means of a dialysis method, a gel filtration method, a fractionation precipitation method, etc.

The thus obtained antigen binds 5 to 60 mols in average of the peptide thereto per mole of a protein and enables one to subsequently prepare an antibody having a high specificity to the antigen. Particularly, antigens to which the peptide is bound in an amount of 5 to 20 mols, preferably 8 to 15 mols, in average, per mole of a protein are preferred since they have higher specificity and enable one to obtain antibodies having high activity and sensitivity.

The preparation of an antibody using the antigen is carried out by administering the aforesaid antigen, preferably using an adjuvant, to mammals to thereby produce a desired antibody in vivo and collecting the antibody. Improved titers can be obtained by repeated injections over a period of time.

While there is no particular limitation to mammals provided for the preparation of antibodies, it is generally preferred to use rabbits or guinea pigs but horses, goats, pigs, rats, cows, sheep, etc., can also be used. In the production of antibodies, a definite amount of the antigen obtained as described above is diluted with a physiological saline solution to a suitable concentration and the resulting dilution is mixed with a complete Freund's adjuvant to prepare a suspension. The suspension is administered to mammals. For example, the aforesaid suspension is intracutaneously administered (0.1 to 5 mg/time as the amount of the antigen) to rabbit. Then the suspension is administered every two weeks over a period of 2 to 10 months, preferably 4 to 6 months, to effect immunization. The collection of the antibody is carried out by collecting blood from the immunized animal after the passage of 1 to 2 weeks subsequent to the final administration, centrifuging the blood and isolating serum from the blood. According to this procedure, an antibody which will selectively complex to the antigenic determinant of the AIDS virus, particularly the p17 gag core protein at positions 92 to 109, can be collected and used as an antisera for immunizing a patient at risk for AIDS (e.g. homosexuals, Haitians, intravenous drug users, and so on), exposed to the AIDS virus, or suffering from the symptoms of AIDS or ARC. Alternatively, the antibodies can be used for assaying for HTLV-III/LAV, ARV-2 and similar human leukemia retroviruses capable of causing AIDS, utilizing RIA, ELISA, etc. For example, when used in a serological assay the antibodies of the present invention can be labelled with a radioactive isotope for use in an RIA or with enzymes or fluorescent substances conventionally used and can be used in ELISA, fluorescence immunoassay (FIA), etc. Further, the antibodies of the present invention can be insolubilized by reacting them with a conventional insolubilizing agent.

The present invention, therefore, provides antigenic thymosin $\alpha_1$ peptides, and p17 gag peptides, including the fragments and analogs thereof which provide powerful vaccines for neutralizing AIDS virus. Therefore, the vaccines of this invention can be used to immunize patients at risk for AIDS, or exposed to the AIDS virus or to treat patients with AIDS-Related Complex or with frank AIDS.

When used as a vaccine in the method of this invention, the vaccine can be introduced into the host most conveniently by injection, intramuscularly, parenterally, orally or subcutaneously. Any of the common liquid or solid vehicles may be employed, which are acceptable to the host and which do not have any adverse side effects on the host nor any detrimental effects on the vaccine. Phosphate buffered saline (PBS), at a physiological pH, e.g. pH 6.8 to 7.2, preferably pH 7, may be used as a carrier, alone or with a suitable adjuvant. The concentration of immunogenic antigen may vary from about 50 to 200, such as about 100 μg per injection, in a volume of solvent generally of from about 0.25 to 1, such as about 0.5 ml. Multiple injections may be required after the initial injections and may be given at intervals of from about 2 to 14 days, for example, about 7 days, when multiple injections are given.

As an alternative to the above described active immunization in which the administration to a host is of the immunogenic antigenic thymosin $\alpha_1$ or related peptides of formula (I) and (II), it is also possible to directly administer to a host the anti-AIDS virus antibodies of this invention, usually raised in a different species than the host, although antibodies raised in a different individual of the same species as the host may also be used. In the case of such passive immunizing antisera, generally the same modes of application and the same types of carriers and the same or higher dosage rates as described for the active immunization method can also be used. For example, as much as 1.5 grams of murine monoclonal antibody can be administered without undue toxicity, provided the antibody is administered slowly (e.g. about 6 hours) by intraveneous infusion.

Still another alternative embodiment within the scope of this invention is a vaccine and immunization method based on an anti-idiotypic antibody raised against a monoclonal antibody to any one of the peptides of formulas (I) and (II) or to thymosin $\alpha_1$. Anti-immunoglobin sera raised against a monoclonal antibody is defined as "anti-idiotype" serum and recognizes the variable region of the eliciting antibody and is directed against the combining site. This anti-idiotype antibody which is directed against the combining site can in fact substitute for the original antigen. Therefore, it is possible to use this mechanism to immunize and raise antibodies against the thymosin $\alpha_1$ or fragments and analogs thereof or the gag peptides and fragments and analogs as, or more, efficiently than via classic immunization protocols.

Figure 2:
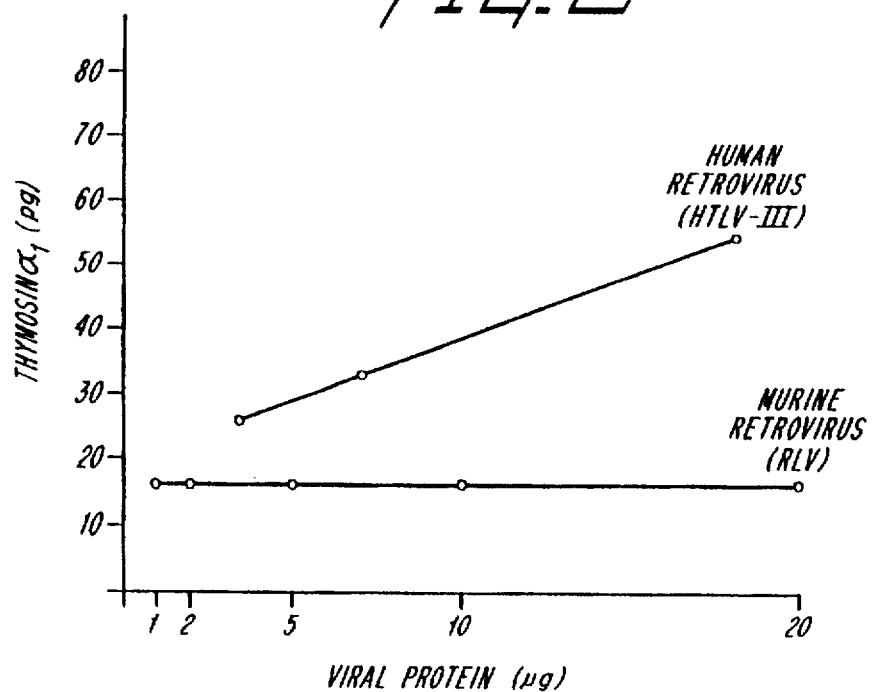
FIG. 2 is a graph of a competitive radioimmunoassay between the human retrovirus HTLV-III/LAV and Rouscher murine leukemia retrovirus (RLV).

As a measure of the specificity of the antibodies to the thymosin $\alpha_1$ peptide for HTLV-III/LAV viral proteins a competitive radioimmunoassay was performed as generally described in the aforementioned U.S. Pat. No. 4,264,571, and in U.S. Pat. No. 4,339,427, the disclosures of which are incorporated herein by reference. It is found that HTLV-III/LAV proteins, but not Rouscher murine leukemia retroviral (RLV) protein, can displace $T\alpha_1$ in the competitive RIA. The results are shown in FIG. 2. HTLV-III/LAV shows a linear dose response curve to $T\alpha_1$ antisera whereas RLV isolate is not cross-reactive with $T\alpha_1$ antisera. These results demonstrate that large amounts of immuno-reactive $T\alpha_1$-like material is present in the HTLV-III/LAV isolate but not in an RLV isolate, thereby confirming that the homologous sequences in HTLV-III/LAV and $T\alpha_1$ are not present in RLV.

Figure 3:
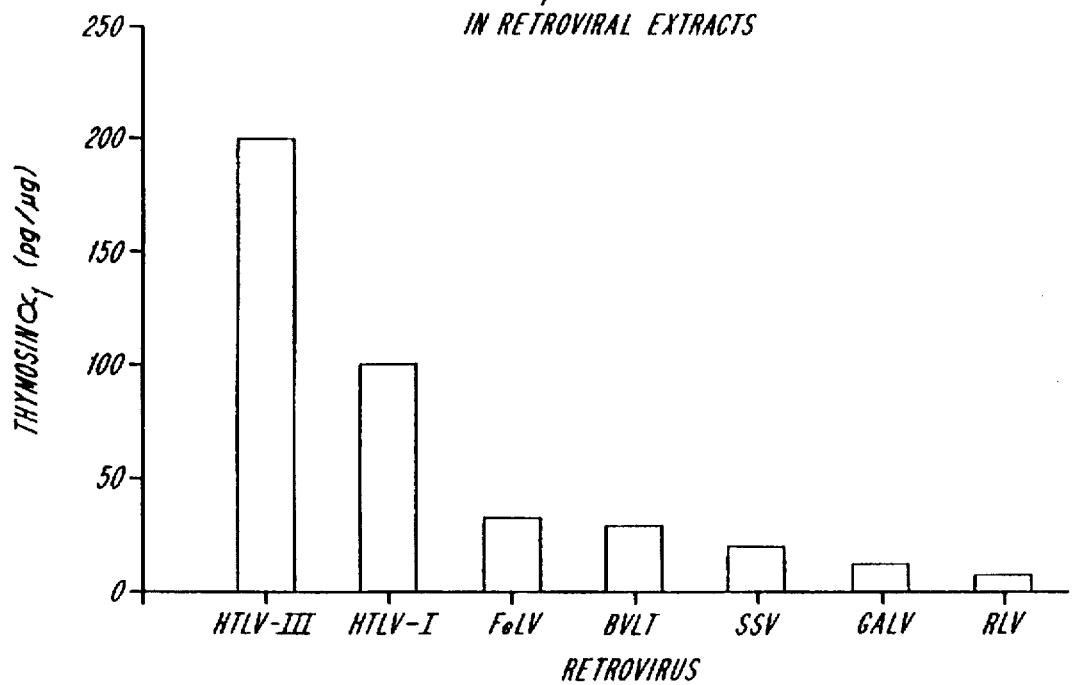
FIG. 3 is a bar graph representing the cross-reactivity determined by RIA for antisera to thymosin $\alpha_1$ to HTLV-III/LAV, HTLV-I and various animal retrovirus extracts.

In order to further demonstrate the specificity of the antibodies to thymosin $\alpha_1$ and the other novel antibodies of this invention to human retrovirus HTLV-III/LAV and similar AIDS-associated retroviruses the cross-reaction of other retroviruses to $T\alpha_1$ were determined by competitive RIA. The results are shown in FIG. 3. None of the feline leukemia retrovirus (FeLV), simian sarcoma retrovirus (SSV), gibbon ape leukemia retrovirus (GALV) or murine leukemia retrovirus (RVL) showed any significant cross-reactivity.

EXAMPLE 1

This example illustrates the solid phase peptide synthesis for the production of one of the novel peptides according to the present invention, namely the [Ser][87] analog of the triacontapeptide corresponding to positions 86–115 of the p17 gag core protein of HTLV-III/LAV, having the formula Tyr—Ser—Val—His—Gln—Arg—Ile—Asp—Val—
Lys—Asp—Thr—Lys—Glu—Ala—Leu—Glu—Lys—
Ile—Glu—Glu—Glu—Gln—Asn—Lys—Ser—Lys—
Lys—Lys—Ala.

Boc—Ala—OCH$_2$—C$_6$H$_4$-Resin (2 g, 1.0 mmol) (Cycle 1) is placed in a peptide synthesis vessel (150 ml) and is treated with 20 volumes of the following solvents and/or reagents, in the following order for each of cycles 2–30:

(1) Pre-wash with 40% trifluoroacetic acid (TFA);
(2) Stir 28 minutes with 40% trifluoroacetic acid (TFA);
(3) Wash 3 times with dichloromethane, $CH_2Cl_2$;
(4) Pre-wash with 10% triethylamine (TEA);
(5) Stir 5 minutes with 10% TEA;
(6) Wash 3 times with $CH_2Cl_2$;
(7) Stir with Boc-Lys(ClZ)-OH (1.25 g, 3 mmol) (Cycle 2) and dicyclohexylcarbodiimide (0.618 g, 3 mmol) for 120 minutes;
(8) Wash three times each with $CH_2Cl_2$, 50% isopropanol and $CH_2Cl_2$. Completion of the coupling reaction is tested by the ninhydrin reaction. If coupling is incomplete, steps (7) and (8) are repeated.

Upon completion of coupling, the next and succeeding synthesis cycles 3–30 are carried out by following steps (1) through (8) using each of the protected (Boc) amino acids in step (7) in sequence, as follows:

Cycle 3: Boc-Lys(ClZ)-OH (1.25 g);
Cycle 4: Boc-Lys(ClZ)-OH (1.25 g);
Cycle 5: Boc-Ser(Bzl)-OH (0.89 g);
Cycle 6: Boc-Lys(ClZ)-OH (1.25 g);
Cycle 7: Boc-Asn-OH (0.70 g)+1-hydroxy benxtriazde (HBT) (0.92 g);
Cycle 8: Boc-Gln-OH (0.74 g)+HBT (0.92 g);
Cycle 9: Boc-Glu(OBzl)-OH (1.01 g);
Cycle 10: Boc-Glu(OBzl)-OH (1.01 g);
Cycle 11: Boc-Glu(OBzl)-OH (1.01 g);
Cycle 12: Boc-Ile-OH (0.72 g);
Cycle 13: Boc-Lys(ClZ)-OH (1.25 g);
Cycle 14: Boc-Glu(OBzl)-OH (1.01 g);
Cycle 15: Boc-Leu-OH (0.75 g);
Cycle 16: Boc-Ala-OH (0.57 g);
Cycle 17: Boc-Glu(OBzl)-OH (1.01 g);
Cycle 18: Boc-Lys(ClZ)-OH (1.25 g);
Cycle 19: Boc-Thr(Bzl)-OH (0.93 g);
Cycle 20: Boc-Asp(OBzl)-OH (0.97 g);
Cycle 21: Boc-Lys(ClZ)-OH (1.25 g);
Cycle 22: Boc-Val-OH (0.65 g);
Cycle 23: Boc-Asp(OBzl)-OH (0.97 g);
Cycle 24: Boc-Ile-OH (0.72 g);
Cycle 25: Boc-Arg(Tos)-OH (1.29 g);
Cycle 26: Boc-Gln-OH (0.74 g)+HBT (0.92 g);
Cycle 27: Boc-His(Tos)-OH (1.23 g);
Cycle 28: Boc-Val-OH (0.65 g);
Cycle 29: Boc-Ser(Bzl)-OH (0.89 g);
Cycle 30: Boc-Tyr(BrZ)-OH (1.49 g).

Following this procedure yields 6.18 grams of the 30 amino acid resin, on a dry basis.

Part of the protected peptide resin (3.5 g) is treated with approximately 15 ml of anhydrous HF at 0° C. in the presence of 5 ml anisole for 45 minutes. Excess acid is evaporated off and the resulting cleaved and deprotected crude peptide is washed briefly with dry ether, and extracted into 150 ml of 2% ammonium acetate. This peptide solution is concentrated to about 40 ml and the concentrated peptide solution is chromatographed on a Sephadex G-10 column (2.6×90 cm) using 0.1M acetic acid as eluent, and monitored at 280 nm.

The major peptide fractions are pooled and concentrated to 50 ml. After freeze drying 1.09 g of substantially pure peptide product, as determined by high pressure liquid chromatography (HPLC), is obtained.

EXAMPLE 2

Radioimmunoassay

A stock solution of synthetic thymosin $\alpha_1$ at concentrations suitable for the working range of the assay (between 0.5 and 37.5 ng/100 µl) is prepared in RIA buffer and frozen at 10° C. The RIA buffer (RIAB) is phosphate buffered saline (pH=7.4, 0.01M sodium phosphate and 0.15M NaCl), to which is added 0.05% (wt/volume) $NAN_3$, 0.01 mM EDTA and 0.5% bovine serum albumin (50 g/l). Nine standards containing 0.5 to 37.5 ng/100 µl of synthetic thymosin $\alpha_1$ are prepared from the stock solutions and frozen at 4° C. for use as needed. Unknown samples require 5–20 µl of serum per assay and saline is added to give 100 µl sample. All tubes are brought to a final volume of 400 µl with RIAB. A 50 µl aliquot of stock antiserum (1/200 dilution) is added to each tube. The dilution gives 20–25% binding of tracer and a final dilution of 1/2000. Nonspecific binding is assessed by processing tubes containing all the assay reagents except the specific anti-thymosin $\alpha_1$ antiserum. The tubes are vortexed and incubated for 24 hours at 4° C. Separation of free from bound tracer is carried out by the addition of KYNAR (goat antirabbit IgG bound to a polymer). After vortexing and incubation for 15 minutes at room temperature the immunoprecipitate is pelleted by centrifugation at 1500×g for 15 minutes at 4° C. The supernatants are aspirated and discarded and the radioactivity in the immunoprecipitates is measured in an automatic gamma spectrometer (Beckman Gamma 4000). The counts per minute for standards and unknowns are corrected for nonspecific background, usually 5% of the total radioactivity, and divided by the corrected counts per minute for reaction tubes in which no competing antigen is introduced (Bo). The data are analyzed on a Beckman system DP 5500 which plots log dose (x axis) vs observed counts and calculates data using the four parameter logistic method in which the dose-response curve is described by:

$$Y = \frac{(A-D)}{1 = (x/c/B + D}$$

where Y=the response, x=the concentration, A=the response when x=0 (Bo), B=a slope factor, c=the dose corresponding o the response halfway between A and B, and D=the response for an infinite concentration.

EXAMPLE 3

Enzyme linked immunosorbent assay—ELISA

A stock solution of synthetic $T\alpha_1$ prepared in phosphate buffered saline at a concentration suitable for the working range of the assay, i.e. 6 dose levels between 100 and 3200 pg/ml is aliquoted, stored at −20° C. and thawed once for preparation of the standard curve. The ELISA buffer is phosphate buffered saline, 8.0 gm of NaCl, 0.2 gm of $KH_2PO_4$, 1.15 gm of $Na_2HPO_4$ and 0.2 gm of KCl to which is added 0.75 ml of Tween 20 and 0.2 gm of $NaN_3$ in 1 liter of distilled water pH 7.4. Standard solutions of synthetic $T\alpha_1$ (500 µl) or unknown samples (250 µl) are added to 12×75 mm test tubes. Buffer, 250 µl, is then added to the unknown samples and 500 µl of a 1:2500 dilution of stock antiserum is added to all tubes. The tubes are vortexed sealed with parafilm and incubated overnight at 4° C. Wells of a Costar flat bottom microtiter plate are coated with synthetic $T\alpha_1$ by adding 100 µl/well of a 50 ng/ml $T\alpha_1$ solution in Dulbecco's phosphate buffered saline (10×, GIBCO, Grand Island, N.Y.) and incubated overnight at 37° C. The plate is washed with PBS/Tween and blocked with 200 µl of horse serum per well. 100 μl of each antibody-antigen solution is added to the wells and incubated overnight at 4° C. The plate is washed and 100 μl of a 1/1000 dilution of biotin labeled anti-rabbit-antibody in PBS-Tween is added to each well and incubated for one hour at 37° C. The plates are washed, 100 μl of avidin alkaline phosphatase (1/3000 dilution in PBS-Tween) is added and plates are incubated for an additional hour. To each well is added 100 μl of phosphate substrate (2 pellets/10 ml of diethanolamine buffer). The plate is incubated over 30 minutes and the OD determined. Values for serum samples are then obtained via calculation of a least squares fit for the standards.

EXAMPLE 4

Monoclonal Antibodies

The production of monoclonal antibodies to thymosin peptides can be carried out as follows using $T\alpha_1$ as an example. The spleens from the mice producing anti-$T\alpha_1$ are fused with SP20/myeloma cells using polyethylene glycol. Hybrid clones are produced using hypoxanthine-aminopterin-thymidine (HAT) selection media and subsequently, clones are identified by RIA and ELISA as described in Examples 2 and 3 as producing antibodies to $T\alpha_1$. The monoclonal hybridomas are maintained in tissue culture and passage into the peritoneal cavity of synegenic mice for ascites production of anti-thymosin $\alpha_1$.

Immunization to obtain the anti-thymosin $\alpha_1$ antibodies are produced as follows: Mice (Balb/c) are injected with $T\alpha_1$ conjugated to mouse IgG. The coupling is via mixing 3.5 mg/ml synthetic $T\alpha_1$ with 7.0 mg/ml mouse IgG (Miles Laboratory, Elkhart, Ind.) and 40 μl of gluteraldehyde for 3½ hours, followed by dialysis overnight against saline. The conjugate is mixed on day 1 with an equal volume of Freund's complete adjuvant and 100 μg/0.1 ml is injected i.p. into 8 mice. Boosts are given at weeks 2 and 4 with 10 μg conjugate $T\alpha_1$ and incomplete Freunds. The mice are bled via tail vein on the 5th week and their serum assessed for anti-thymosin $\alpha_1$ via ELISA. Briefly, 5 ng of $T\alpha_1$ is plated in each well of a microtiter plate and various dilutions of mouse sera added and incubated for one hour. After washing, anti-mouse IgG coupled to alkaline phosphatase is added, incubated for 1 hour, washed and substrate added. Four days prior to removal of spleen for the fusion, the mice are boosted with 20 μg, i.p. or i.v. of thymosin. IgG conjugate.

Fusion is performed as follows: The cells for fusion (8-azaguanine resistant SP20 myelomas) are brought into log phase by daily passage for 5 days prior to the fusion. Spleens from the mice are harvested, washed with RPMI and resuspended to give equal volumes with the myeloma cells ($10^8$/ml). Both cells are mixed and pelleted at 600×g. The supernatant is removed and 1 ml of 50% polyethylene glycol at 37° C. is added gently over a 1-minute time period. Cells are mixed an additional minute, 8 mls of warm DMEM added slowly, and the cells are pelleted. The cells are resuspended at $2\times10^6$/ml and 0.1 ml added to each well of a microtiter plate. Media is exchanged as needed (RPMI with 20% fetal bovine serum). After 14 days, HT medium is used and the wells of interest screened for antibody using the ELISA and RIA.

The wells testing positive are then subject to limiting dilution with conditioned HT media until monoclonicity could be assured. They are retested using both the RIA and ELISA and are maintained in both tissue culture and ascites of synergenic mice primed with 0.5 ml pristan 1-3 weeks prior to receiving the hybrid. By harvesting ascites a sufficient quantity of material from which to concentrate the monoclonal antibody is obtained.

EXAMPLE 5

Production of the gag polypeptide by genetic engineering using *E. coli*

Either the entire p17 gag coding sequence (to produce the entire gag protein of HTLV-III/LAV or ARV) which extends from the methionine codon to the glutamine codon or any shortened coding sequence extending over at least the nucleotides encoding for the amino acids extending from position 92, the isoleucine codon, to position 109, the asparagine codon, can be expressed under the control of the hybrid tryp/lac promoter-operator in *E. coli*. The polypeptide can then be induced by IPTG, an inducer of the lac operon.

The introduction of an appropriate set of transcription and translation signals can be done by introducing a NcoI site at the starting (e.g. methionine) codon and then adding a specialized repression vector such as PMFZO1Tet which includes the hybrid tryp/lac promotor, lac operator and a strong ribosome binding sequence located such that the methionine in the adjacent NcoI site is optimally located for translation of transcribed mRNA and the entire coding sequence will be translated efficiently in *E. coli*.

Hybrid B gal-GAG fusion polypeptides are produced using appropriate restriction endonuclease generated fragments of the DNA inserted into the gene for galactosidase near either the $NH_2$ terminus or the COOH terminus. The frame constructs are identified by gal enzyme activity in the colonies. These proteins are purified by affinity chromatography using the affinity of B galactosidase for substrate analogs.

EXAMPLE 6

This example demonstrates the efficiency of the novel gag polypeptides of this invention to elicit production of serum antibodies in rabbits.

The synthetic gag triacontapeptide of Example 1 is coupled to Keyhole Limpet Hemocyanin (KLH) by means of glutaraldehyde using the following procedure. Equivalent amounts (dry weight) of each protein, triacontapeptide and hymocyanin, are dissolved in 0.25M $NAPO_4$, pH 7.0 buffer at a concentration of 2 mg/ml. Equal volumes of the protein solutions are mixed, and a volume of glutaraldehyde (25% aqueous solution) equal to 1% of the volume of the protein mixture is added. The reaction is allowed to continue for 3 hours while being stirred at room temperature. The reaction mixture is diluted in sterile saline to a final concentration of the triacontapeptide of 100 μg/ml. The solution of coupled polypeptide is aliquoted and stored at –20° C.

The mixture of products resulting from the crosslinking reactions carried out at room temperature is not fractionated or purified in any way. The KLH conjugate is diluted with sterile normal saline and stored frozen for immunizations.

Rabbits were immunized by administering 100 μg polypeptide (as the KLH conjugate) in emulsion with Freund's Complete Adjuvant at 15–20 intradermal sites on the back of each rabbit according to the method of Vaitukaitis et al., J. Clin. Endoch. 33,988 (1971). Weekly boosts of 10 μg polypeptide per animal in Freund's Incomplete Adjuvant were also administered at multiple intradermal sites. Titers of antibody against the peptide which were usable in the ELISA as described above in Example 3 were obtained following a rest period of only 3 weeks, subsequent boosting with 100 μg amounts of polypeptide and bleeding of each rabbit 7 days following each boosting dose.

Figure 4:
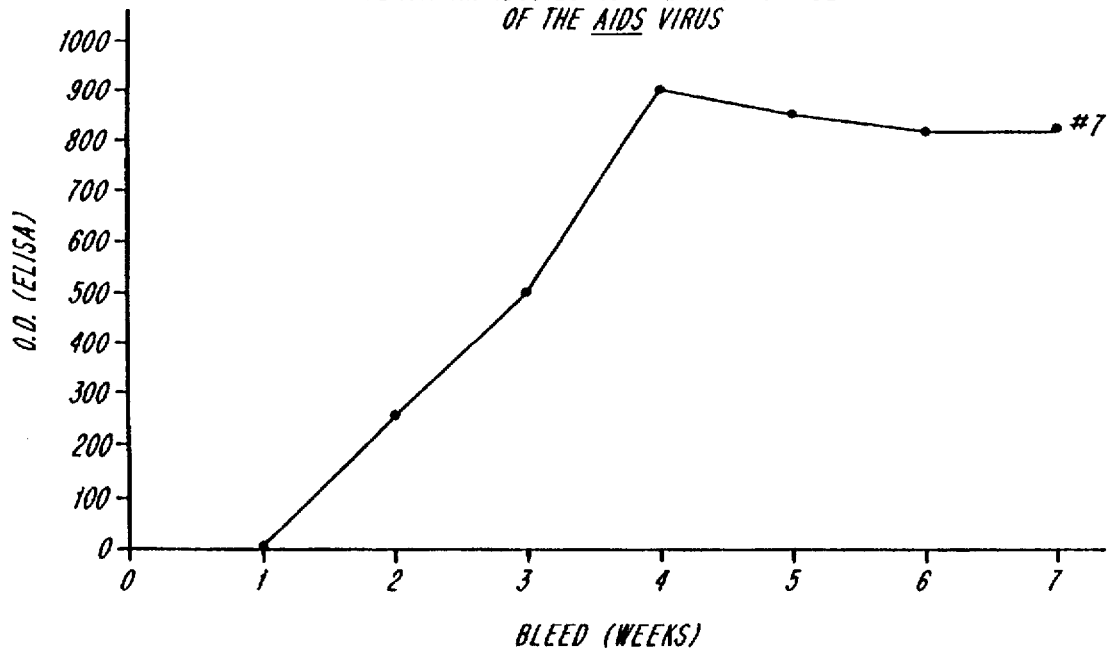
FIG. 4 is a graph representing a typical antibody response in rabbits to vaccination with one of the novel gag proteins of this invention.

The serum from each rabbit is diluted 1:10 with PBS and assayed via the ELISA assay as described in Example 3. The results for the rabbit having the highest antibody titer is shown in FIG. 4 where week 1 represents the pre-bleed value. The maximum concentration of antibody is found at week 4.

What is claimed is:

1. A method for detection of HIV antigen in body fluids of human patients which comprises contacting a sample of the body fluid with a polyclonal or monoclonal antibody to a peptide fragment of the p17 protein of HIV-1 and having up to about 40 amino acids including the amino acid sequence of the formula Ile-$Y_1$-$Y_2$-Lys-Asp-Thr-Lys-Glu-Ala-Leu-$Y_3$-Lys-Ile-Glu-Glu-Glu-Gln-Asn
wherein $Y_1$ is Asp or Glu, $Y_2$ is Val or Ile, $Y_3$ is Glu or Asp, and measuring the formation of antigen-antibody complexes by radioimmunoassay, enzyme-linked immunosorbent assay or indirect immunofluorescent assay.

2. The method of claim 1 wherein the method of measuring the formation of antigen-antibody complex is radioimmunoassay using $^{125}$I as the radiolabelled isotope.

3. The method of claim 1 wherein the method of measuring the formation of antigen-antibody complex is enzyme-linked immunosorbent assay.

4. A diagnostic test kit for detection of HIV antigen in human body fluid comprising an enclosure containing multiwell plates which are coated with antibodies to an antigenic peptide fragment of the p17 gag protein of HIV-1 and having up to about 40 amino acids and comprising the sequence Ile-$Y_1$-$Y_2$-Lys-Asp-Thr-Lys-Glu-Ala-Leu-$Y_3$-Lys-Ile-Glu-Glu-Glu-Gln-Asn
wherein $Y_1$ is Asp or Glu, $Y_2$ is Val or Ile, $Y_3$ is Glu or Asp, and ELISA materials for enzyme detection including normal animal antisera and enzyme, labelled anti-antibody antisera and a color change indicator.

5. A diagnostic kit for serological detection of HIV antigen in human fluid samples using radioimmunoassay comprising, a container, a cover, and within said container, labelled antigenic material and antibodies to the HIV, and means to detect antibody-antigen reaction complexes, wherein said antigenic material is a peptide fragment of p17 protein of HIV-1 having up to about 40 amino acids and comprising the sequence Ile-$Y_1$-$Y_2$-Lys-Asp-Thr-Lys-Glu-Ala-Leu-$Y_3$-Lys-Ile-Glu-Glu-Glu-Gln-Asn
wherein $Y_1$ is Asp or Glu, $Y_2$ is Val or Ile, $Y_3$ is Glu or Asp, and the antibody to HIV are antibodies to said peptide fragment.

6. The diagnostic kit of claim 5 wherein said detection means comprises an antibody reactive to said antibodies to the HIV.

7. A diagnostic kit for the serological detection of HIV antigen in human fluid samples using Western or Immuno Blot procedure comprising a container, a cover, and within said container a blotting membrane and polyacrylamide slab gel and sodium dodecyl sulfate, and additionally one or more surfactants, pH modifiers and blocking reagent, detection means for detecting antibody-antigen reaction complex formulation, and antibodies which will recognize the antigenic determinants of the p17 core protein of HIV present in said fluid sample, said antibodies being to a peptide fragment of the p17 protein of HIV-1 and having up to about 40 amino acids and comprising the sequence Ile-$Y_1$-$Y_2$-Lys-Asp-Thr-Lys-Glu-Ala-Leu-$Y_3$-Lys-Ile-Glu-Glu-Glu-Gln-Asn
wherein $Y_1$ is Asp or Glu, $Y_2$ is Val or Ile, $Y_3$ is Glu or Asp.

8. The diagnostic kit of claim 7 wherein said detection means comprises dilute normal serum from a first animal and a radioactively labelled antibody which recognizes said normal serum.

9. A method for the assay of HIV antigen in a sample, which method comprises mixing said sample with a known amount of labelled peptide and an antibody which will selectively complex with said HIV antigen, separating the resulting antibody-antigen complex from uncomplexed labelled peptide, measuring the degree of binding of said labelled peptide in said complex and determining the amount of HIV antigen present in said sample by comparing said degree of binding to a standard curve obtained by mixing known amounts of HIV antigen with fixed amounts of said labelled peptide and said antibody, and determining the degree of binding for each known amount of HIV antigen, said labelled peptide comprising a peptide fragment of up to about 40 amino acids of the p17 protein of HIV-1 comprising at least the sequence Ile-$Y_1$-$Y_2$-Lys-Asp-Thr-Lys-Glu-Ala-Leu-$Y_3$-Lys-Ile-Glu-Glu-Glu-Gln-Asn
wherein $Y_1$ is Asp or Glu, $Y_2$ is Val or Ile, $Y_3$ is Glu or Asp, and said antibody comprising antibodies to a peptide sharing common epitopes with the HIV antigen in the amino acid sequence extending over the region of the p17 gag protein including from at least about position 92 to at least about position 109.

10. The method of claim 9 wherein a radioimmunoassay is employed and radiolabelled peptide is used.

11. The method of claim 10 wherein said radiolabelled peptide is the triacontapeptide having the formula

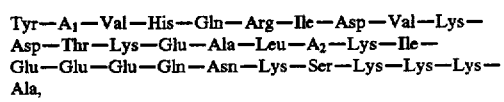

where $A_1$ is Cys or Set and $A_2$ is Asp or Glu.

12. The method of claim 9 which further comprises separating the antibody-antigen complex from the sample by a double antibody technique using a second antibody immunologically reactive against the serum of the host animal in which the HIV antigen specific antibody was elicited.

* * * * *